United States Patent [19]

Sakakibara et al.

[11] Patent Number: 4,833,156
[45] Date of Patent: May 23, 1989

[54] TREATING AMNESIA WITH A PYRROLIDONE DERIVATIVE

[75] Inventors: Masayuki Sakakibara; Yuzi Munezuka; Shinichiro Kato, all of Maebashi, Japan

[73] Assignee: Kirin Beer Kabushiki Kaisha, Tokyo, Japan

[21] Appl. No.: 160,600

[22] Filed: Feb. 26, 1988

[30] Foreign Application Priority Data

Feb. 28, 1987 [JP] Japan .................. 62-46474

[51] Int. Cl.$^4$ .................................. A61K 31/40
[52] U.S. Cl. .................................... 514/424
[58] Field of Search ......................... 514/424

[56] References Cited

FOREIGN PATENT DOCUMENTS 138721 10/1984 European Pat. Off. .

*Primary Examiner*—Stanley J. Friedman
*Attorney, Agent, or Firm*—Ladas & Parry

[57] ABSTRACT

A use of the pyrrolidone derivative represented by the following formula [I] as an anti-amnesitc agent:

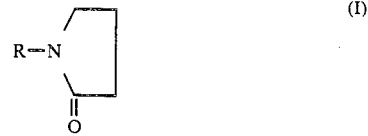

(I)

wherein R represents a group

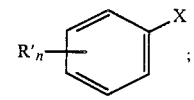

X represents —SO$_2$— or —CO—; R' represents a hydrogen atom, a lower alkyl group, a trifluoromethyl group, a halogen atom or a nitro group; n denotes an integer of 1–5; and, when n is an integer of 2 or more, R' may be the same or different, provided that (a) when X is —SO$_2$—, there is no case where R' is 3-CF$_3$, 4-Cl-5-CF$_3$, 3,5-(CF$_3$)$_2$ or 3-NO$_2$;
(b) when X is —CO—, there is no case where n denotes 1 or 2 and R' is a halogen atom or a nitro group;
(c) when X is —SO$_2$—, there is no case where n denotes 1 or 2 and R' is a group other than 4-Cl or 3-NO$_2$; and
(d) when n denotes 2, there is no case where the groups R' represent the same group which is halogen atom or a nitro group.

Typical pyrrolidone derivatives are N-(4'-toluene-sulfonyl)-2-pyrrolidone, N-(4'-chlorobenzenesulfonyl)-2-pyrrolidone, N-benzenesulfonyl-2-pyrrolidone and N-[4'-(1'', 1''-dimethylethyl)benzoyl]-2-pyrrolidone, particularly N-(4'-chloro-benzenesulfonyl)-2-pyrrolidone.

3 Claims, 3 Drawing Sheets

TREATING AMNESIA WITH A PYRROLIDONE DERIVATIVE

BACKGROUND OF THE INVENTION

Field of the Art

The present invention relates to a use of a pyrrolidone derivative as an anti-amnestic agent.

Recently there has begun an aging of the human population in many places, and thus the problem of senile dementia has become serious year by year. Accordingly, if a medication could be developed in order to suppress or lessen the dementic symptoms, it would be a great boon to the society because of its usefulness. Such a medication includes calcium hopantenate (Hopate), Calan, aniracetam, piracetam and the like, but the effects of these medications have not always been defined clearly. Accordingly, the development of a medication which evinces anti-amnestic activity more definitely has been eagerly desired.

SUMMARY OF THE INVENTION

We have aggressively studied on inhibitors to proline specific endopeptidase for the purpose of developing a medication having the aforementioned pharmaceutical activity. As a result, we have found that some pyrrolidone compounds are more potent than aniracetam here used as a standard substance.

Thus, the anti-amnestic agent according to the present invention contains as an active ingredient a pyrrolidone derivative represented by the following formula [I];

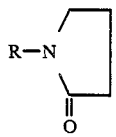
(I)

wherein: R represents a group

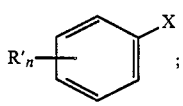
;

X represents $-SO_2-$ or $-CO-$; R' represents a hydrogen atom, a lower alkyl group, a trifluoromethyl group, a halogen atom or a nitro group; n denotes an integer of 1 to 5; and when n is an integer of 2 or more R' may be the same or different, provided that (a) when X is $-SO_2-$, there is no case where R' is 3-$CF_3$, 4-Cl-5-$CF_3$, 3,5-$(CF_3)_2$ or 3-$NO_2$;

(b) when X is $-CO-$, there is no case where n denotes 1 or 2 and R' is a halogen atom or a nitro group;

(c) when X is $-SO_2-$, there is no case where n denotes 1 or 2 and R' is a group other than 4-Cl or 3-$NO_2$; and (d) when n denotes 2, there is no case where the groups R' represent the same group which is a halogen atom or a nitro group.

The pyrrolidone derivative which is an active ingredient of the anti-amnestic agent according to the present invention has an anti-amnestic activity more effective than aniracetam which is known as an anti-amnestic agent.

PYRROLIDONE DERIVATIVES

Figure 1:
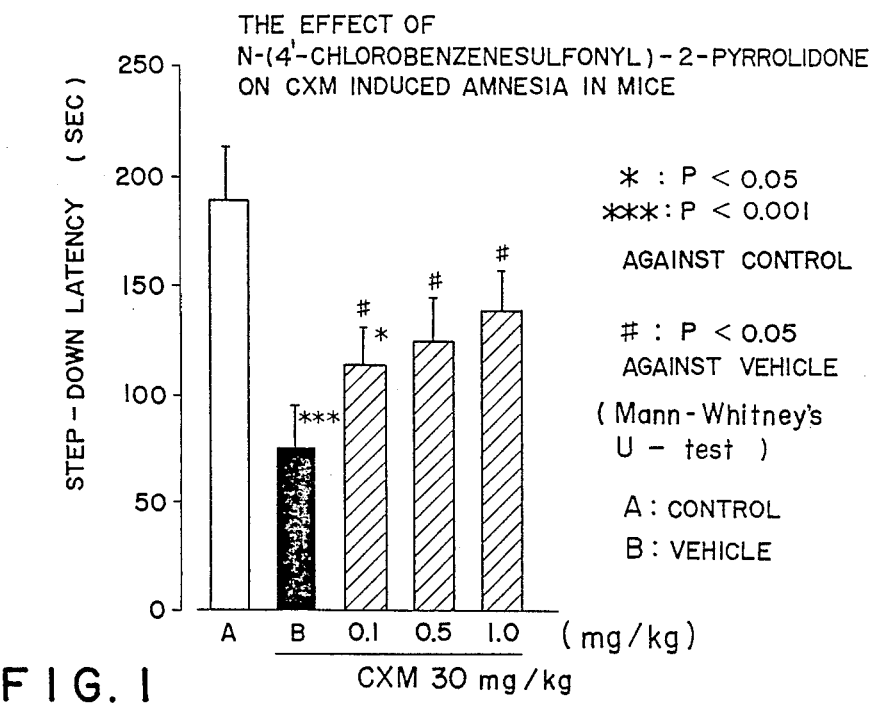
FIG. 1 is a graph indicating effects of N-(4'-chlorobenzenesulfonyl)-2-pyrrolidone on cycloheximide (hereinafter referred to as CXM)-induced amnesia in mice.
Figure 2:
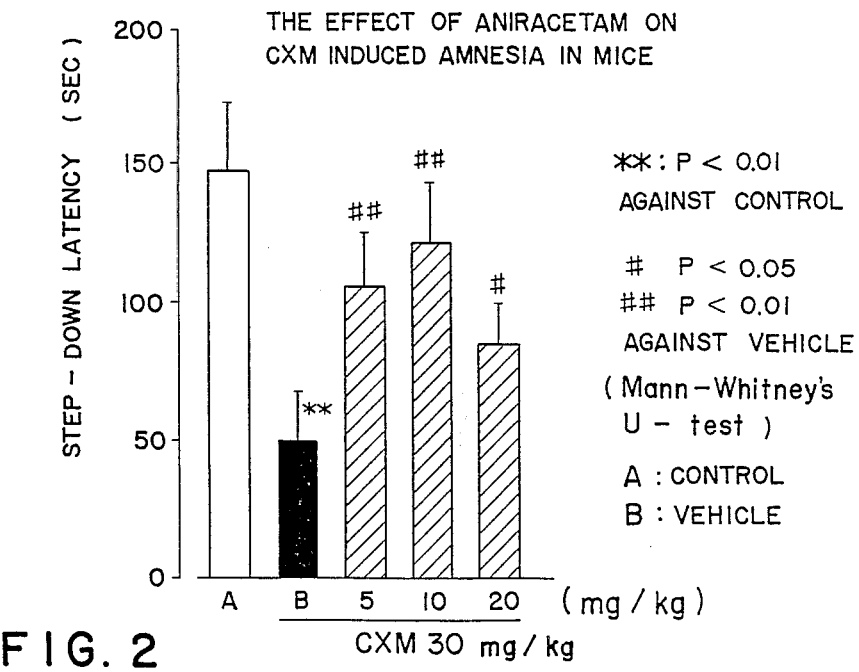
FIG. 2 is a graph indicating effects of aniracetam on CXM-induced amnesia in mice.

The pyrrolidone derivative used as an effective ingredient of the anti-amnestic agent according to the present invention is represented by the formula [I] described above.

Specific examples of the compounds represented by the formula [I] are:

(a) N-(4'-toluenesulfonyl)-2-pyrrolidone,
(b) N-(4'-chlorobenzenesulfonyl)-2-pyrrolidone,
(c) N-benzenesulfonyl-2-pyrrolidone, and
(d) N-[4'-(1'',1''-dimethylethyl)benzoyl]-2-pyrrolidone, among which the compound (b) is preferred.

These compounds are well-known and described in Chemical Abstract with Registry Nos. 10019-95-1, 73096-15-8, 88000-68-4 and 73665-30-2, respectively. The first two of these are also disclosed in Japanese Patent Application Laid-Open No. 153763/80.

PREPARATION OF THE COMPOUND

The pyrrolidone derivative (I) according to the present invention may be prepared by an optional method suitable for the object.

Preparation Method A

One of the specific preparation methods comprises providing the R- moiety and the pyrrolidone moiety of the compound of the formula (I) respectively from separate compounds and coupling them, and specifically it includes the reaction of a compound R-Z wherein Z represents a halogen atom and N-trimethylsilyl-2-pyrrolidone.

This process can be carried out in accordance with the method of M. SAKAKIBARA et al.: Agric. Biol. Chem., 37(5), 1131 (1973).

The reaction is ordinarily carried out by the use of an appropriate solvent, but when the reaction proceeds slow, it can be made rapid by conducting it in the absence of solvents. The solvents used for the reaction may be any inert solvents which will not participate in the reaction. Preferable examples are: aromatic hydrocarbons such as benzene, toluene, and xylene, and the like; halogenated hydrocarbons such as methylene chloride, chloroform and carbon tetrachloride; ethers such as diethyl ether, dioxane and tetrahydrofuran; ketones such as acetone and methyl ethyl ketone; esters such as ethyl acetate; acetonitrile; and dimethylformamide used singly or as a mixture thereof. The amount of the solvent used is not critical and is generally used in an amount of 0 to 20 times those of the raw materials used.

The reaction temperature is not critical and generally ranges from 0° C. to 150° C. The reaction is generally completed in 30 minutes to 24 hours. In some cases, unreacted raw materials may be recovered, even if the reaction is continued further.

Although the reaction ordinarily proceeds even in the absence of a catalyst, addition of an organic base such as triethylamine, pyridine, N-methyl-morpholine or dimethylaniline may accelarate it in the case where it proceeds too slow.

The isolation of the compound from the obtained reaction mixture and the purification thereof are usually carried out by using the techniques common to the instant field of organic synthetic chemistry.

Preparation Method B

Another specific preparation method comprises forming a pyrrolidone moiety from a linear structure, a proto-type of a pyrrolidone moiety, in the precursor for the compound represented by the formula (I) by cyclization reaction, specifically by the condensation-cyclization reaction of a compound R—NH—(CH$_2$)$_3$—COOH in the presence of an appropriate condensation agent.

This process can be carried out in accordance with the method disclosed in Japanese Patent Application Laid-Open No. 153763/80.

The condensation agents used herein are preferably dicyclohexylcarbodiimide (DDC), chlorocarbonate esters, onium salts and the like. In order to accelerate the reaction, an organic base such as triethylamine, dimethylaniline, N-methyl-morpholine, pyridine, N-methylpiperidine, or N-methylpyrrolidine may be added to the reaction. The solvents used for the reaction may be any inert solvents which will not participate in the reaction and will readily dissolve the raw materials and reagents. Preferable solvents are: aromatic hydrocarbons such as benzene, toluene, and xylene; halogenated hydrocarbons such as methylene chloride, chloroform, dichloroethane, and carbon tetrachloride; and esters such as ethyl acetate, used singly or as a mixture thereof. The reaction proceeds rapidly at a temperature of $-10°$ C. to 50° C. and is ordinarily completed in 30 minutes to 24 hours. The solvent is usually used in an amount of 1 to 20 times that of the raw materials.

The product is generally isolated from the reaction mixture by subjecting it to isolation and purification procedures which are generally employed in the instant field of organic synthetic chemistry.

Use of the Compound

The pyrrolidone derivative represented by the formula (I) is useful as an anti-amnestic agent.

More specifically, the compound exhibits an anti-amnestic activity by inhibiting the activity of proline specific endopeptidase, and the inhibitory effect is more intensive than that of aniracetam which is a conventionally well-known anti-amnestic agent.

There have already been reported several works with reference to the anti-amnestic effects of proline specific endopeptidase inhibitory agents [such as (a) Shin Kubota, Tohru Nakajima, Shunichi Okada, Tetsuo Hayashi and Keiji Nakamura: Abstracts of the Reports in the 56th Meeting of the Pharmacological Society of Japan, 141 (1983); (b) Tadashi Yoshimoto, Nobuhiro Kohriyama, Kunio Kaku, Hiroshi Oyama and Daisuke Tsuru: Abstracts of the Reports in the 59th Meeting of the Biochemical Society of Japan, 621 (1986); (c) Tadashi Yoshimoto, Kenichi Tsukumo, Hiroshi Matsubara and Daisuke Tsuru: Abstracts of the Reports in the 56th Meeting of the Biochemical Society of Japan, 831 (1983); (d) Japanese Patent Application Laid-Open No. 37764/1986.]

A pyrrolidone derivative represented by the formula (I) can be formulated into preparations and administered in the same manner as the anti-amnestic agents such as aniracetam and the like. It may be administered through either oral or perenteral route such as injection. It is generally formulated into a preparation by incorporating an appropriate carrier or diluent (e.g. pyrogen free distilled water, starch and the like). It is also possible to formulate into a preparation by blending the compound (I) or an anti-amnestic agent comprising the said compound with a compatible physiologically active substance or medicament.

Although the dosage should be determined by the judgement of a doctor for individual patients, it may be said that the compound can be administered in a dosage lower than that of well-known aniracetam based on their proline specific endopeptidase inhibitory effects. The typical dosage may be 0.1 to 10 mg/kg body weight.

The present invention is described in more detail by referring to the following examples, which are all illustrative of preferred embodiments of and not to limitative of the present invention.

Synthetic Example 1

To a solution of 7.6 g of tosyl chloride (0.04 mole) and 6.9 g of N-trimethylsilyl-2-pyrrolidone (0.044 mole) in 50 ml of anhydrous tetrahydrofuran was added 0.2 ml of triethylamine, and the mixture was stirred at 90° C. for 16 hours. The solvent was removed under vacuum, and the residue was dissolved in 50 ml of chloroform. To this solution was added 15 g of silica gel (Wako Gel C-200), and then chloroform was removed under vacuum. The powdery residue was suspended in a mixed solvent of hexane-ethyl acetate (3:2), and the suspension was subjected to chromatography on a column (D 40 mm × L 500 mm) of 300 g of silica gel (Wako Gel C-200) eluted with a mixed solvent of hexane-ethyl acetate (3:2). The crystalline product thus obtained was recrystallized from a mixture of chloroform-ether to give 2.98 g of N-(4'-toluenesulfonyl)-2-pyrrolidone as colorless crystals.

(a) mp: 144.5° to 145.5° C.

(b) IR$\nu_{max}^{KBr}$ (cm$^{-1}$): 3550 (m), 3460 (s), 3410 (s), 3240 (w), 3100 (w), 3050 (w), 3000 (w), 2950 (w), 2900 (w), 1925 (w), 1730 (s), 1685 (w), 1638 (w), 1618 (w), 1598 (m), 1490 (m), 1475 (m), 1419 (w), 1395 (w), 1385 (w), 1350 (s), 1320 (w), 1295 (m), 1240 (m), 1215 (s), 1200 (s), 1180 (s), 1160 (s), 1115 (s), 1085 (m), 1067 (w), 1020 (m), 960 (s), 882 (w), 838 (w), 813 (s), 798 (w), 710 (s), 700 (w), 660 (s), 640 (w), 600 (s), 560 (s), 545 (s), 530 (s), 490 (w), 440 (w).

(c) $^1$H-NMR (100 MHz, CDCl$_3$)δ: 2.04 (quintet, J=7 Hz, 1H), 2.07 (quintet, J=7 Hz, 1H), 2.43 (t, J=7 Hz, 1H), 2.44 (s, 3H), 2.45 (t, J=7 Hz, 1H), 3.90 (t, J=7 Hz, 2H), 7.34 (d, J=8 Hz, 2H), 7.93 (d, J=8 Hz, 2H).

(d) Elementary analysis: Calculated for $C_{11}H_{13}NO_3S$; C: 55.21, H: 5.48, N: 5.85, Found; C: 55.44, H: 5.60, N: 5.77.

(e) FDMS (m/z): 239 (M+).

SYNTHETIC EXAMPLE 2

In 10 ml of chloroform was suspended 2.57 g of N-(4'-toluenesulfonyl)-4-aminobutyric acid (0.01 mole), and 1.21 g of triethylamine (0.012 mole) was added dropwise to the mixture with stirring on a water bath at ca. 20° C. While the mixture thus obtained was stirred on an ice-salt bath, a solution of 1.41 g of ethyl chlorocarbonate (0.013 mole) in 2 ml of chloroform was added dropwise at ca. 20° C. After completion of addition, stirring was continued for further 2 hours, and the reaction was diluted with 15 ml of ethyl acetate, washed sequentially with water (5 ml×2), 1N HCl (5 ml) and water (5 ml×2), and dried over anhydrous sodium sulfate. The solution was filtered, and the solvent was removed under reduced pressure. The residue thus obtained was recrystallized from a mixed solvent of chloroform-ether to give 2.37 g of N-(4'-toluenesulfonyl)-2-pyrrolidone as colorless crystals. Physical properties were identical with those in Synthetic Example 1.

SYNTHETIC EXAMPLE 3

To a solution of 8.4 g of 4-chlorobenzenesulfonyl chloride (0.04 mole) and 6.9 g of N-trimethylsilyl-2-pyrrolidone (0.044 mole) in 50 ml of anhydrous tetrahydrofuran was added 0.2 ml of trimethylamine, and the mixture was stirred at the reflux temperature for 30.5 hours. The solvent was removed from the reaction under reduced pressure, and the residue was dissolved in 50 ml of chloroform. After addition of 15 g of silica gel (Wako Gel C-200) to the solution, chloroform was again removed under reduced pressure. The powdery residue thus obtained was supended in a mixed solvent of hexane-ethyl acetate (7:3). The suspension was subjected to chromatography on a column (D 40 mm×L 500 mm) of 300 g of silica gel (Wako Gel C-200). Elution with a mixed solvent of hexane-ethyl acetate (7:3) followed by a mixed solvent of hexane-ethyl acetate (3:2) gave a crystalline product, which was recrystallized from a mixed solvent of chloroform-ether to give 5.83 g of N-(4'-chlorobenzenesulfonyl)-2-pyrrolidone as crystals.

(a) mp: 155°-155.5° C. (mp: 150°-151° C., which is disclosed in Japanese Patent Application No. 153763/80), (b) IR $\nu_{max}^{KBr}$ (cm$^{-1}$): 3440 (s), 3100 (w), 3080 (w), 3000 (w), 2950 (w), 2900 (w), 1920 (w), 1900 (w), 1740 (s), 1730 (s), 1690 (w), 1640 (w), 1620 (w), 1585 (m), 1570 (w), 1560 (w), 1490 (w), 1480 (m), 1460 (w), 1397 (m), 1350 (s), 1310 (w), 1280 (m), 1210 (m), 1190 (m), 1180 (s), 1118 (s), 1085 (s), 1080 (s), 1020 (m), 1010 (m), 955 (s), 882 (w), 835 (m), 820 (m), 758 (s), 710 (m), 615 (s), 590 (s), 535 (s), 475 (m).

(c) $^1$H-NMR (100 MHz, CDCl$_3$) δ: 2.10 (quintet, J=7 Hz, 2H), 2.46 (t, J=7 Hz, 2H), 3.91 (t, J=7 Hz, 2H), 7.52 (d, J=8 Hz, 2H), 8.00 (d, J=8 Hz, 2H).

(d) Elementary analysis: Calculated for $C_{10}H_{10}NClO_3S$; C: 46.24, H: 3.88, N: 5.39, Found; C: 46.50, H: 3.96, N: 5.45.

(e) FDMS (m/z): 259 (M+).

SYNTHETIC EXAMPLE 4

In 20 ml of tetrahydrofuran was dissolved 2.78 g of N-(4'-chlorobenzenesulfonyl)-4-aminobutyric acid (0.01 mole). To the stirred solution on an ice bath was added 2.06 g of dicyclohexylcarbodiimide (0.01 mole), and the mixture was stirred at 0° C. for 21 hours. The reaction mixture was filtered, and the solid material was washed with anhydrous tetrahydrofuran. The filtrate and the washings were combined, and tetrahydrofuran was removed under reduced pressure. The residue thus obtained was recrystallized from a mixed solvent of chloroform-ether to give 2.37 g of N-(4'-chlorobenzenesulfonyl)-2-pyrrolidone as crystals. Physical properties were identical with those in Synthetic Example 3.

SYNTHETIC EXAMPLE 5

To 7.06 g of benzenesulfonyl chloride (0.04 mole) was added 6.9 g of N-trimethylsilyl-2-pyrrolidone (0.044 mole), and the mixture was stirred at the reflux temperature for 30 minutes. The reaction mixture was subjected to chromatography on a column (D 40 mm×L 250 mm) of 150 g of silica gel (Wako Gel C-200). Elution with a mixed solvent of hexane-ethyl acetate (3:2) gave a crystalline product, which was recrystallized from a mixed solvent of chloroform-ether to give 3.34 g of N-benzenesulfonyl-2-pyrrolidone as colorless crystals.

(a) mp: 83° C., (b) IR $\nu_{max}^{KBr}$ (cm$^{-1}$): 3550 (s), 3470 (s), 3420 (s), 3240 (m), 3070 (w), 3000 (w), 2990 (w), 2930 (w), 1920 (w), 1900 (w), 1730 (s), 1640 (m), 1620 (m), 1585 (w), 1485 (m), 1465 (w), 1453 (m), 1418 (w), 1357 (s), 1340 (m), 1322 (m), 1290 (w), 1283 (m), 1241 (m), 1215 (s), 1198 (m), 1175 (s), 1118 (s), 1095 (s), 1075 (m), 1020 (m), 997 (w), 965 (s), 930 (w), 895 (w), 840 (w), 750 (m), 738 (s), 698 (w), 685 (s), 670 (w), 645 (m), 600 (s), 580 (s), 545 (s), 535 (m).

(c) $^1$H-NMR (100 MHz, CDCl$_3$) δ: 2.08 (quintet, J=7 Hz, 2H), 2.44 (t, J=7 Hz, 2H), 3.91 (t, J=7 Hz, 2H), 7.61 (m, 3H), 8.06 (m, 2H).

(d) Elementary analysis: Calculated for $C_{10}H_{11}NO_3S$; C: 53.32, H: 4.92, N: 6.22, Found; C: 53.20, H: 4.82, N: 6.11.

(e) FDMS (m/z): 226 (M+).

SYNTHETIC EXAMPLE 6

To 100 ml of anhydrous methylene chloride were added 2.43 g of N-benezenesulfonyl-4-aminobutyric acid (0.01 mole), 4.0 g of 2-chloro-1-methylpyridinium iodide and 3.0 g of triethylamine, and the mixture was stirred at the reflux temperature for 8 hours. A 50 ml portion of 10% aqueous potassium carbonate was added to the reaction, and the mixture was extracted with chloroform. The organic layer was washed with brine and dried over anhydrous sodium salfate. The solvent was removed under reduced pressure. The residue was subjected to chromatography on a column (D 40 mm×L 200 mm) of 120 g of silica gel (Wako Gel C-200). Elution with a mixed solvent of hexane-ethyl acetate (3:2) to give 2.15 g of N-benzenesulfonyl-2-pyrrolidone as colorless crystals. Physical properties were identical with those in Synthetic Example 5.

INHIBITION OF PROLINE SPECIFIC ENDOPEPTIDASE ACTIVITY

The inhibitory effects of the compounds represented by the formula (I) were determined by measuring the residual peptidase activity. The experimental procedure was agreed with the method by Tadashi Yoshimoto and Daisuke Tsuru: Tanpakushitsu, Kakusan and Koso, 29 (2), 127 (1984).

The results are shown in the following table. A residual activity of the peptidase for a well-known aniracetam used as a standard is also shown in the table.

| Synthetic Examples | Compounds | Residual Activity |
|---|---|---|
| — | Aniracetam | 89.5 |
| 1,2 | CH₃—⟨benzene⟩—SO₂N(pyrrolidone) | 47.4 |
| 3,4 | Cl—⟨benzene⟩—SO₂N(pyrrolidone) | 51.3 |
| 5,6 | ⟨benzene⟩—SO₂N(pyrrolidone) | 51.3 |

MEASUREMENT OF ANTI-AMNESTIC EFFECT

1. Mouse Step-Down Test

1—1. Method

The test was carried out in accordance with the method described by Nabeshima et al.: Psychopharmacology, (1986) 89, 334–337. That is, a wooden platform (4×4×4 cm) was placed in the center on a floor of a stainless steel grid (30×30 cm), and the whole apparatus was surrounded with clear acrylic resin plates. In acquisition test, a mouse (ddY, male, 5 to 6 week old) was placed on the platform, and electric stimulus was applied for 20 seconds immediately after the mouse stepped down on the grid. Then the mouse was taken out of the apparatus and cycloheximide hydrochloride (30 mg/kg) was administered subcutaneously in order to induce amnesia. In the retention test, the mouse was again placed on the platform, and the time before the mouse stepped down on the grid was measured as the step-down latency. N-(4'-chlorobenzenesulfonyl)-2-pyrrolidone and aniracetam were individually suspended in 0.3% Tween 80 and administered orally at 20 minutes before acquisition test.

1-2 Results

As shown in FIG. 1, N-(4'-chlorobenzenesulfonyl)-2-pyrrolidone significantly remitted the cycloheximide induced amnesia in a dosage of 0.1–1.0 mg/kg. Aniracetam showed an effectiveness in a dosage of 5–20 mg/kg.

2. Rat Delayed-Matching Test 2-1 Method

An apparatus equipped with two lever switches on the respective sides of the front face of the inside of an operant experimental box (25×31×33 cm), red lamps just above respective levers and a white lamp at a further upper position was used for the experiment. A rat bred under restricted feeding (SD, male, 150 to 300 g) was placed in the apparatus. Either one of the red lamps arranged on the right and left sides was lit for 5 seconds, and, at a specific time (delayed time) after it was turned off, the white lamp at the center was lit. The system of the apparatus was so set that if the lever which was at the side of the red lamp having lit was pushed, a feed pellet (ca. 50 mg) was given as a correct choice, and if another lever was pushed no pellet was given as an incorrect choice. After the training had been conducted to ensure that, in the test of delay time being 0.1 sec, the correct choice rate was maintained at the level of 80% or more for three consecutive days, the test was conducted. In the test, delay times were set at 0.1, 4, 16 and 32 seconds, and, at each of the delay times, 6 runs were conducted at random (24 runs in total, 1 run/minute). The test was started after 10 minutes of subcutaneous administration of 0.06 mg/kg of (-)-scopolamine hydrochloride to obtain an amnestic rat which showed a low level of the correct selection rate compared with a control administered with a physiological saline. N-(4'-chlorobenzenesulfonyl)-2-pyrrolidone and aniracetam were administered orally in the form of suspensions in 0.3% Tween 80 at 20 minutes before test.

2-2 Results

Figure 3:
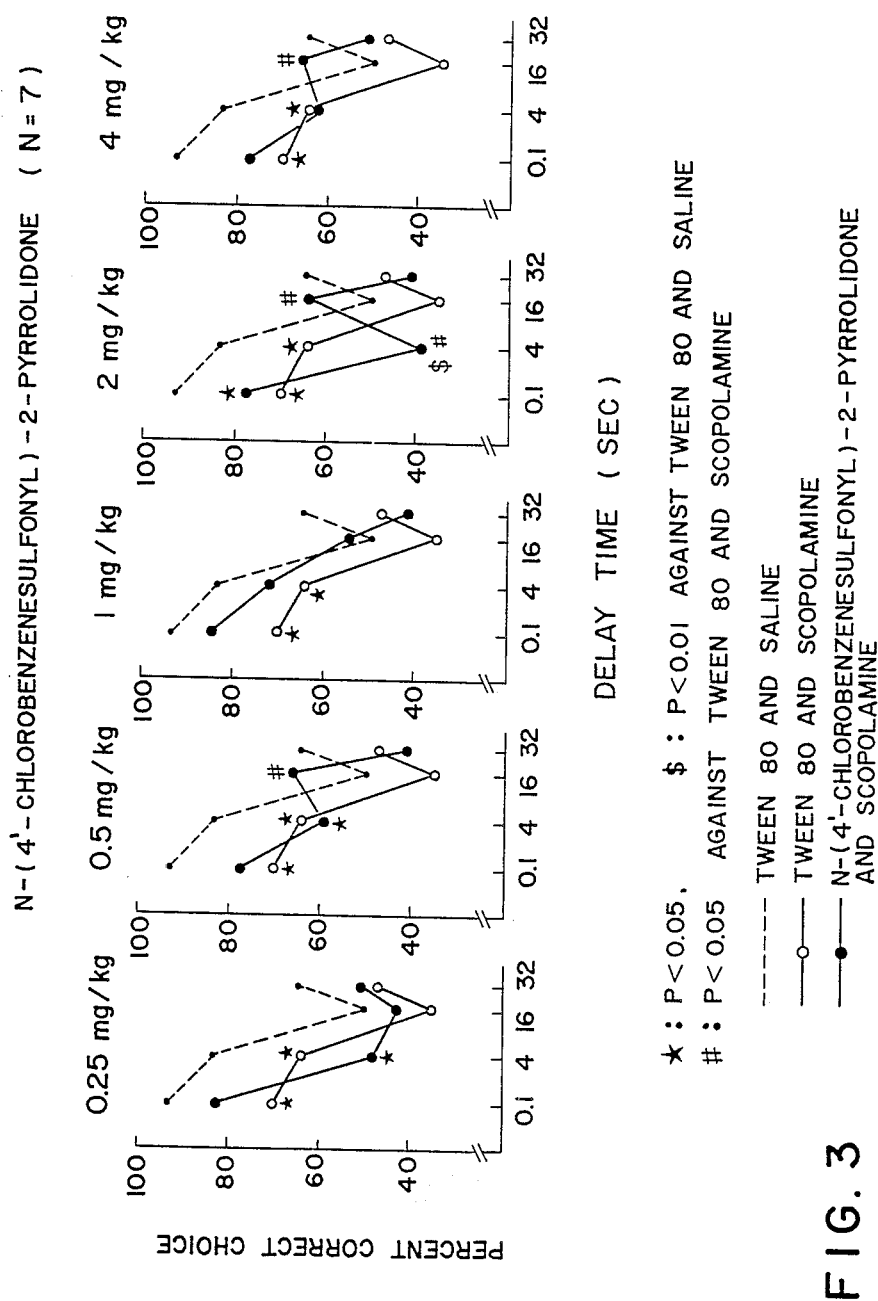
FIG. 3 is a group of graphs indicating effects of intragastically administered N-(4'-chlorobenzenesulfonyl)-2-pyrrolidone on delayed discrimination response in rats, N-(4'-chlorobenzenesulfonyl)-2-pyrrolidone (or Tween 80) being administered 20 min before, and scopolamine (or saline) being administered 10 min before the start of the test session, respectively.
Figure 4:
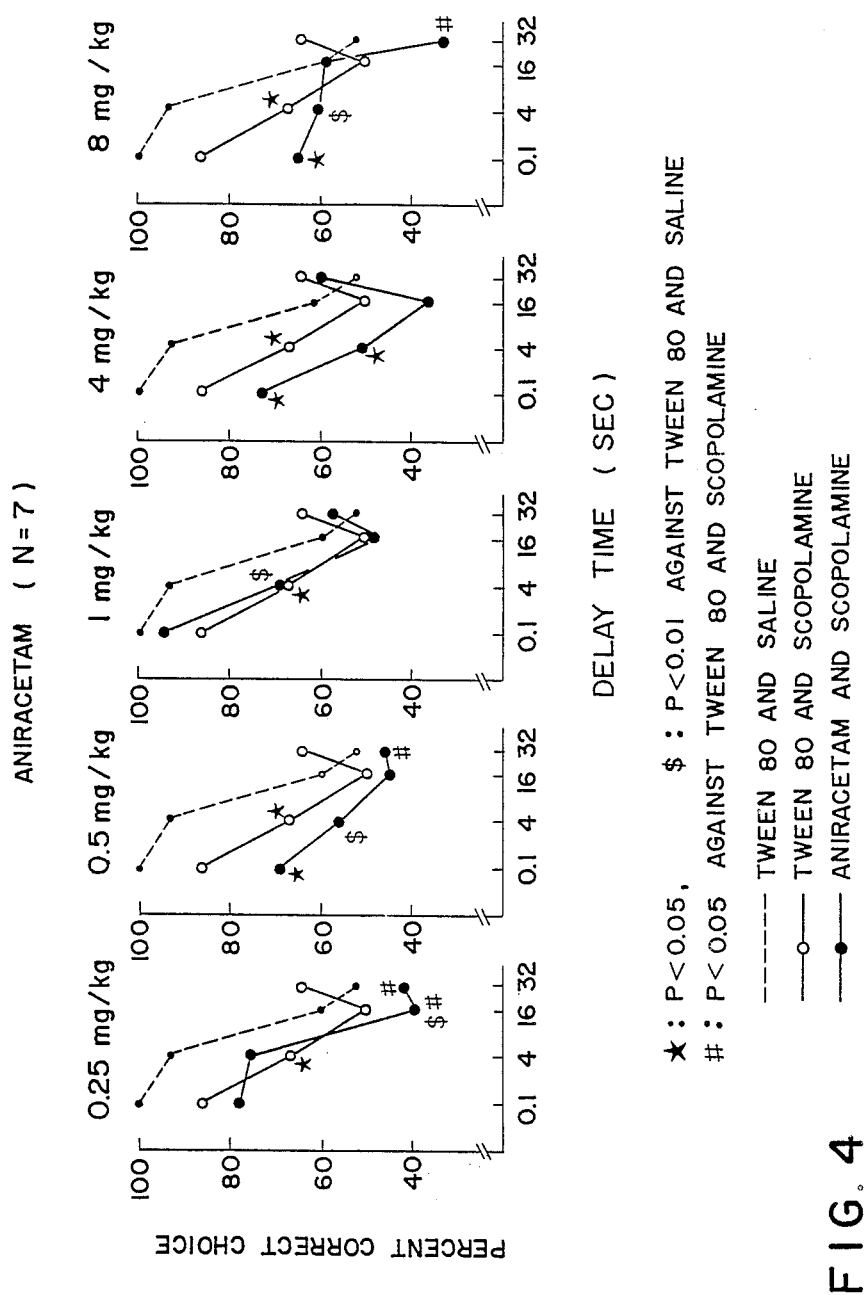
FIG. 4 is a group of graphs indicating effects of intragastically administered aniracetam on delayed discrimination response in rats, aniracetam (or Tween 80) being administered 20 min before and scopolamine (or saline) being administered 10 min before the start of the test session, respectively.

As shown in FIG. 3, N-(4'-chlorobenzenesulfonyl)-2-pyrrolidone showed remission of scopolamine induced amnesia at several dosages and delay times. On the other hand, aniracetam did not remitted at all scopolamine induced amnesia as shown in FIG. 4.

3. Conclusion

In either case of the above-described tests, N-(4'-chlorobenzenesulfonyl)-2-pyrrolidone exhibited an anti-amnestic effect and was more effective than aniracetam.

ACUTE TOXICITY

Acute toxicity was evaluted by oral administration of the compounds to ddY male mice (7 week old).

High level of safety was confirmed for N-(4'-chlorobenzenesulfonyl)-pyrrolidone according to the present invention because of its $LD_{50}$ being 2000 mg/kg or more.

We claim:

1. A process for treating amnesia, comprising administering to a patient having amnesia a pharmaceutically effective quantity of a pyrrolidone derivative represented by the following formula:

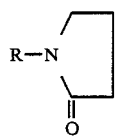

wherein: R represents a group

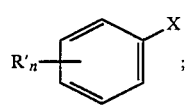

X represents —SO₂— or —CO—; R' represents a hydrogen atom, a lower alkyl group, a trifluoromethyl group, a halogen atom or a nitro group; n denotes an integer of 1 to 5; and when n is an integer of 2 or more R' may be the same or different, provided that (a) when X is —6 SO₂—, there is no case where R' is 3-CF₃, 4-Cl-5-CF₃, 3,5-(CF₃)₂ or 3-NO₂;

(b) when X is —CO—, there is no case where n denotes 1 or 2 and R' is a halogen atom or a nitro group;

(c) when X is —SO$_2$—, there is no case where n denotes 1 or 2 and R' is a group other than 4-Cl or 3-NO$_2$; and
(d) when n denotes 2, there is no case where the groups R' represent the same group which is a halogen atom or a nitro group.

2. A process according to claim 1 wherein the compound represented by the formula [I] is selected from the group consisting of N-(4'-toluenesulfonyl)-2-pyrrolidone, N-(4'-chlorobenzenesulfonyl)-2-pyrrolidone, N-benzenesulfonyl-2-pyrrolidone and N-[4'-(1'',1''-dimethylethyl)benzoyl]-2-pyrrolidone.

3. A process according to claim 2 wherein the compound represented by the formula [I] is N-(4'-chlorobenzenesulfonyl)-2-pyrrolidone.

* * * * *